(12) United States Patent
Nettuno et al.

(10) Patent No.: US 11,236,043 B2
(45) Date of Patent: Feb. 1, 2022

(54) AMMONIA-UREA INTEGRATED PROCESS AND PLANT

(71) Applicant: Casale SA, Lugano (CH)

(72) Inventors: Francesco Nettuno, Saronno (IT); Luca Rugnone, Como (IT); Raffaele Ostuni, Lugano (CH)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 16/489,090

(22) PCT Filed: Feb. 1, 2018

(86) PCT No.: PCT/EP2018/052474
§ 371 (c)(1),
(2) Date: Aug. 27, 2019

(87) PCT Pub. No.: WO2018/158026
PCT Pub. Date: Sep. 7, 2018

(65) Prior Publication Data
US 2020/0002273 A1  Jan. 2, 2020

(30) Foreign Application Priority Data

Feb. 28, 2017 (EP) .................................. 17158315

(51) Int. Cl.
*C07C 273/10* (2006.01)
*C01B 3/02* (2006.01)
*C01B 3/52* (2006.01)

(52) U.S. Cl.
CPC ............ *C07C 273/10* (2013.01); *C01B 3/025* (2013.01); *C01B 3/52* (2013.01);
(Continued)

(58) Field of Classification Search
None
See application file for complete search history.

(56) References Cited

U.S. PATENT DOCUMENTS 3,310,376 A     3/1967 Cook et al.
3,640,052 A  *  2/1972 Konoki ................. C07C 273/10
                                                       95/12
(Continued)

OTHER PUBLICATIONS

International Search Report issued in connection with PCT/EP2018/052474, dated Apr. 10, 2018.
(Continued)

*Primary Examiner* — Amy C Bonaparte
(74) *Attorney, Agent, or Firm* — Akerman LLP

(57) ABSTRACT

A process for the production of ammonia and urea in an ammonia-urea integrated plant comprising an ammonia section and a tied-in urea section, wherein a hydrocarbon is reformed to produce ammonia make-up synthesis gas; said make-up gas is purified by shift conversion and removal of carbon dioxide; carbon dioxide is removed from the make-up gas by a first and a second CO2 removal sections; the first section removes CO2 by absorption with a suitable medium, and the second section removes CO2 by washing with a carbamate solution taken from the urea section; the make-up gas is reacted to produce ammonia; the CO2 removed from the make-up gas and at least part of the ammonia are used to produce urea.

9 Claims, 4 Drawing Sheets

(52) U.S. Cl.
CPC .................. *C01B 2203/025* (2013.01); *C01B 2203/0233* (2013.01); *C01B 2203/0283* (2013.01); *C01B 2203/0415* (2013.01); *C01B 2203/068* (2013.01); *C01B 2203/1241* (2013.01); *C01B 2203/142* (2013.01); *C01B 2203/146* (2013.01)

(56) References Cited

U.S. PATENT DOCUMENTS

| | | | |
|---|---|---|---|
| 4,320,103 A | 3/1982 | Pagani | |
| 5,736,116 A * | 4/1998 | LeBlanc | C01B 3/025 423/359 |
| 6,340,451 B1 * | 1/2002 | Pagani | C01C 1/0488 423/359 |
| 7,642,377 B1 * | 1/2010 | Singh | C01B 21/12 422/187 |
| 2004/0028595 A1 | 2/2004 | Davey et al. | |
| 2010/0016635 A1 * | 1/2010 | Singh | C01B 21/12 564/66 |

OTHER PUBLICATIONS

International Preliminary Report on Patentability issued in connection with PCT/EP2018/052474, dated Jun. 3, 2019.
Meessen, Jozef H., "Urea", Ullmann's Encyclopedia of Industrial Chemistry, 2012, Wiley-VCH Verlag GmbH & Co., pp. 665-679.

* cited by examiner

AMMONIA-UREA INTEGRATED PROCESS AND PLANT

This application is a national phase of PCT/EP2018/052474, filed Feb. 1, 2018, and claims priority to EP 17158315.6, filed Feb. 28, 2017, the entire contents of both of which are hereby incorporated by reference.

FIELD OF THE INVENTION

The present invention relates to the field of integrated production of ammonia and urea.

PRIOR ART

An ammonia/urea integrated plant comprises an ammonia section where ammonia is synthesized and a urea section where at least part of said ammonia is reacted with carbon dioxide to produce urea.

In the ammonia section, ammonia is synthesized from a make-up gas of hydrogen and nitrogen. Said make-up gas is produced by reforming a hydrocarbon feed such as natural gas.

The production of the ammonia make-up gas usually comprises steps of primary and secondary reforming and purification by shift conversion, removal of carbon dioxide and optionally methanation. The carbon dioxide removed from the make-up gas can be used in the tied-in urea section for production of urea.

The carbon dioxide is typically removed from the ammonia make-up gas by a physical-chemical absorption in a suitable medium such as aqueous solution of an alkanolamine. The absorption produces a CO2-rich solution which is then regenerated with flashing and/or stripping of the solution. Accordingly, the process requires at least an absorbing column and a regeneration tower, which are large and expensive items.

After purification the make-up gas is compressed to the ammonia synthesis pressure in a multi-stage compressor, commonly referred to as main syngas compressor.

The ammonia synthesis pressure is considerably higher than the pressure of the make-up gas delivered by the front-end. For example the syngas is produced at around 15-30 bar and the ammonia synthesis pressure is 80 to 300 bar. Hence the main syngas compressor is also an expensive item and its stages are aerodynamically highly loaded, to reduce their number. The syngas compressor is normally driven by a gas or steam turbine, preferably by a direct coupling.

The synthesis of urea normally includes: reaction of ammonia and carbon dioxide in a high pressure urea synthesis section to form a urea aqueous solution, and subsequent treatment of said solution (reaction effluent) in at least one urea recovery section at a lower pressure, to recover unconverted matter. The urea recovery section produces a solution containing ammonium carbamate (carbamate solution) which is recycled to the urea synthesis section.

Integration of ammonia and urea production is disclosed e.g. in U.S. Pat. No. 4,320,103.

In recent times, an incentive to build ammonia plants of a large capacity, or to increase capacity of the existing plants, has emerged. The capacity denotes the amount of ammonia that is or can be synthesized in the ammonia section.

When an increase of capacity is sought, however, the main syngas compressor and the CO2 removal section are major bottlenecks.

The required larger flow rate through the syngas compressor may be incompatible with the appropriate compression rate and/or with the direct coupling with the turbine. For example direct coupling is not possible when the necessary compression power would require a turbine so large to be unable to reach the elevated speed of the compressor. A complete new design or revamping of the main syngas compressor and turbine is very expensive.

The CO2 removal section, on the other hand, requires columns of a large diameter whose transportation and erection are problematic.

To summarize, the maximum capacity is substantially limited by the capacity of the synthesis gas compressor-turbine assembly and by the physical-chemical removal of CO2. In most of the commercial ammonia plants, the maximum capacity is around 2'100 MTD (metric tons per day) of ammonia.

A further bottleneck is the ammonia synthesis loop and converter.

SUMMARY OF THE INVENTION

The aim of the present invention is to overcome the aforementioned drawbacks and limitations of the prior art concerning ammonia/urea plants. In particular, the invention aims to reach a large capacity of the ammonia section overcoming the bottlenecks of the main compressor of the make-up synthesis gas and of the CO2 removal section.

These objects are achieved with a process according to claim 1. Preferred embodiments are disclosed in the dependent claims.

The invention provides that the purification of the ammonia make-up gas includes a first step of CO2 removal and a second step of CO2 removal which are carried out in series or in parallel; one of said first and second CO2 removal steps comprises washing CO2-containing make-up gas with a carbamate solution taken from the urea recovery section of the urea plant and preferably also with ammonia taken from the ammonia plant; the carbon dioxide feed for urea synthesis comprises at least part of the carbon dioxide separated from said CO2 removal steps.

A carbamate solution withdrawn from the urea recovery section is used, according to the invention, as a means to remove carbon dioxide from the ammonia make-up gas. This can be made in a washing stage which is in parallel or in series with another stage which operates conventionally, e.g. by absorption.

The capacity of the carbamate solution to absorb CO2 from the CO2-contaning make up gas depends on the technology of the urea process. In some embodiments, the capacity to absorb CO2 is further increased by feeding the CO2 absorption unit, in addition to the carbamate solution, with any of: liquid ammonia, gaseous ammonia, water, ammonia-water solution. Ammonia for this purpose can be taken directly from the ammonia process or from the urea process. For example ammonia can be taken from a recovery and recycle stage of the urea process, if provided.

The ammonia make-up gas is obtained for example by reforming of a hydrocarbon feedstock. Said reforming may include for example: primary reforming with steam and secondary reforming with an oxidant, e.g. with air, oxygen or enriched air, or auto-thermal reforming (ATR).

The CO2 removal can be preceded or followed by other steps of purification. The CO2 removal is preferably performed after a shift conversion of CO to CO2. After the CO2 removal, the make-up gas may be further purified for example by means of a methanation step. The washed gas may contain oxygen, which may need to be suitably removed. In some embodiments the gas is washed with water to remove traces of ammonia, before methanation.

The arrangement in series of the CO2 removal steps means that the effluent of the first CO2 removal step is subsequently treated in the second CO2 removal steps. In some embodiments, a portion of the CO2-containing make-up gas bypasses the first step and is sent directly to the second step.

When the CO2 removal steps are performed in series, the step of washing with the carbamate solution is preferably the first step of the series, because it benefits of a higher partial pressure of carbon dioxide in the gas.

When the CO2 removal steps are in parallel, the portion of CO2-containing make-up gas admitted to the absorption step is preferably greater than the portion admitted to washing with carbamate solution. In some embodiments, at least 70% of the total amount of gas is treated by absorption.

In some embodiments, the CO2 removal steps are performed after a preliminary compression of the CO2-containing make-up gas, which is then elevated at an intermediate pressure between the pressure of production of the ammonia make-up gas (e.g. reforming pressure) and the much higher pressure of ammonia synthesis. The higher CO2 partial pressure enables better separation from the syngas by reaction with the carbamate solution and with ammonia. More preferably, said preliminary compression is performed in one stage or some of the stages of the main syngas compressor. Preferably the preliminary compression is such to have a partial pressure of the CO2 of at least 10 bar. Preferably said compression is carried out downstream of the shift conversion, more preferably after cooling.

In the carbamate washing step, the carbamate solution can be used as it is (i.e. as it is drawn from the urea recovery section), or mixed with an aqueous solution of ammonia recovered from a purge gas of the ammonia loop, according to different embodiments. Preferably the carbamate solution is mixed with liquid or gaseous ammonia with the aim to increase the CO2 absorption capability of the solution. In some embodiments, a portion of the carbamate solution obtained in the recovery section is recycled directly to the urea synthesis, and a remaining portion is used in the purification of the ammonia syngas. After contacting the syngas, the carbamate solution discharged from the washing stage can be sent back to the urea synthesis section.

The carbamate solution is taken from a urea recovery section. In the urea recovery section, an aqueous solution of urea containing unconverted ammonium carbamate may be subject to decomposition, e.g. by heating the solution, obtaining vapours of ammonia and carbon dioxide and a more concentrated solution of urea. The vapours are then condensed to form a so-called carbamate solution. This carbamate can have different composition depending on the original technology of the urea process and by consequence the solution will have different absorption capability of the CO2 in the CO2-containing make up gas. Further details of the synthesis of urea and recovery can be found e.g. in Meessen J. H., "Urea", Ullmann's Encyclopedia of Industrial Chemistry, Wiley-VCH Verlag.

According to a further preferred embodiment, the conversion of the purified make-up gas into ammonia is carried out in at least two synthesis loops arranged in series.

The make-up gas is partially converted in a first (main) synthesis loop obtaining a first ammonia stream and a first stream of unreacted make-up gas. Said unreacted make-up gas is further converted in a second synthesis loop obtaining a second ammonia stream and a second stream of unreacted make-up gas.

The unreacted make-up leaving the second loop is preferably split in two portions. A first portion is recycled back to the main synthesis loop for further reaction and the remaining portion is sent to a purge recovery unit producing at least one stream containing recovered hydrogen and at least one aqueous ammonia solution.

Said at least one stream containing recovered hydrogen is preferably joined with the effluent of the methanator. Said aqueous ammonia solution is preferably used as a further washing agent for removing CO2 from the second portion of gas, as above mentioned.

The advantages of the invention are the following.

The invention enhances the integration and the synergy between the ammonia synthesis and the urea synthesis in integrated ammonia-urea production, using a part of the carbamate solution produced in the urea section as an absorbent to remove carbon dioxide from the make-up gas for the synthesis of ammonia, and using the so liberated carbon dioxide as a reactant for urea.

It has to be noted that the CO2 captured with the carbamate solution needs no compression to the urea synthesis pressure, thereby entailing significant energy savings and CO2 compressor debottlenecking. The majority or all of the captured CO2 is actually in the form of liquid carbamate and just needs to be pumped at the urea synthesis pressure reducing drastically the energy needed for the pressurization if compared to the gas compression.

The invention obtains this benefit without the drawback of poor flexibility, which is typical of the prior art ammonia-urea integrated processes. In particular, the ammonia section can operate during startup or temporary shutdown of the urea section, e.g. for maintenance.

The invention is also attractive for revamping of plants. For example when the capacity of a ammonia-urea plant is increased the amount of ammonia make-up gas may exceed the capacity of the available CO2 removal section, usually a CO2 absorption section. In such a case, the invention provides that the additional amount of syngas can be treated for CO2 removal by washing with some carbamate solution withdrawn from the urea recovery section. A carbamate washing stage is also less expensive than a conventional absorption section since it does not need a regeneration section.

Another advantage in case of a revamping is that the conventional CDR section need not be modified or revamped, since the additional capacity in terms of CO2 removal is given by adding a carbamate washing section. If the existing section cannot cope with the total volumetric flow rate of make-up gas, said new section is installed in parallel.

An advantage of the preliminary compression of the CO2-containing gas pressurized CO2 removal is the increase of the CO2 partial pressure in the CDR section and, consequently, a more efficient separation of carbon dioxide and a reduced size of the related equipment. The preliminary compression has advantages also because of the greater suction pressure of the low-pressure stage of the main syngas compressor, which receives the syngas before CO2 removal.

In some embodiments, thanks to said preliminary compression, a physical absorption of CO2 (instead of chemical) can be applied. It can be appreciated that said compression is synergistic with the above mentioned parallel removal of CO2 by washing with carbamate solution, since both features contribute to debottlenecking the conventional CDR section.

An advantage of the above described arrangement of two ammonia synthesis loops is that the capacity can be increased while the size of the ammonia reactors can be contained to within limits of fabrication.

The invention allows the achievement of a large capacity, even beyond 3'000 MTD, in a cost-effective manner. As a matter of fact, the invention overcomes the major bottlenecks of the main syngas compressor, the CDR section and the synthesis loop.

An ammonia section of an ammonia-urea integrated plant and a method for revamping related a related ammonia section according to the attached claims are also object of the present invention.

DETAILED DESCRIPTION OF PREFERRED EMBODIMENTS

Figure 1:
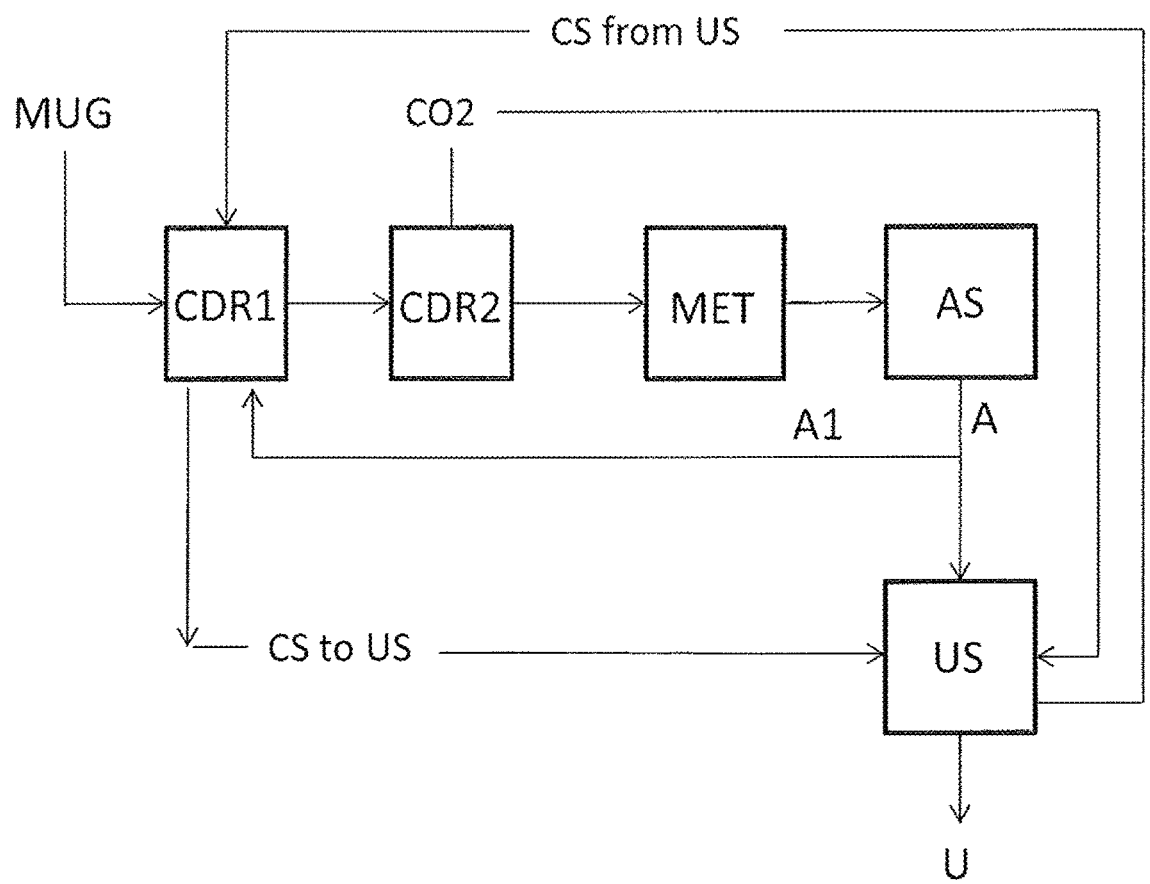
FIG. 1 is a scheme of an embodiment of the invention.

Referring to FIG. 1, ammonia make-up gas MUG e.g. from a shift converter of a reforming section (not shown) is directed to a CO2 removal section comprising CO2 removal stages CDR1 and CDR2. Said stages are arranged in series, so that the effluent of the stage CDR1 feeds the subsequent stage CDR2.

The make-up gas leaving the second stage CDR2 is further purified by methanation MET and feeds ammonia synthesis AS.

The ammonia A feeds directly a urea section US together with carbon dioxide CO2 removed from the syngas in stage CDR2. A part of the ammonia produced in the ammonia section (stream A1) is fed to the CO2 removal section CDR1. The urea synthesis US produces urea U.

The first stage CDR1 operates by washing the syngas with a carbamate solution CS taken from a urea recovery section within the urea synthesis US. For example the solution CS is obtained after decomposition of an aqueous solution of urea produced in a urea reactor or urea synthesis loop. The carbamate solution CS is added with ammonia A1 in the section CDR1 in order to increase the CO2 absorption capability.

The carbamate solution CS, plus the carbon dioxide removed from the syngas, are withdrawn from the stage CDR1 (i.e. after washing the syngas) and are sent again to the urea section US. Preferably all the carbon dioxide removed from the syngas in said stage CDR1 is recycled to the urea section.

The second stage CDR2 operates for example by absorption of carbon dioxide in a suitable medium which is then conveniently regenerated to desorb the gaseous carbon dioxide.

Figure 2:
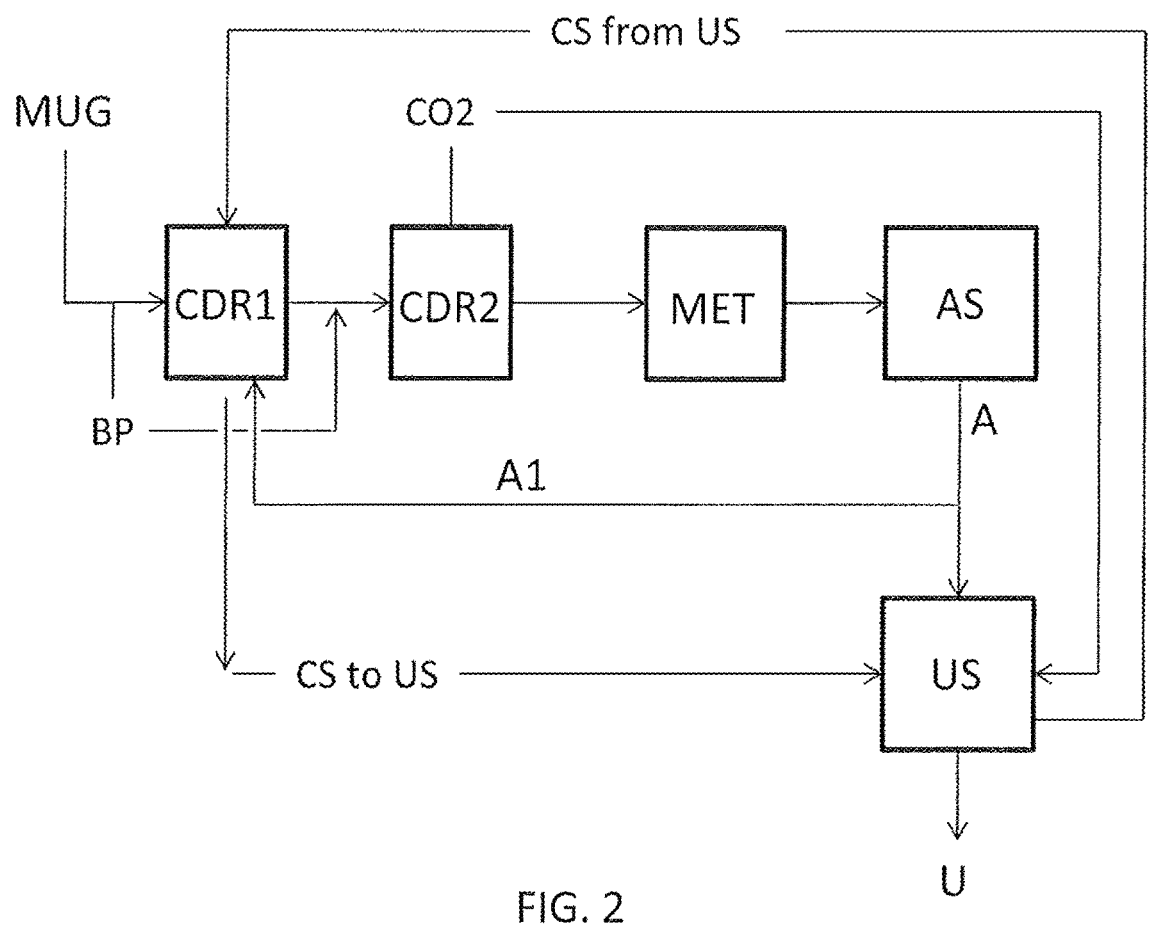
FIG. 2 is a scheme of a second embodiment of the invention.

FIG. 2 shows an embodiment similar to FIG. 1, including a bypass line BP to allow some of the make-up gas MUG to bypass the first stage CDR1 and be admitted directly to the second stage CDR2.

Figure 3:
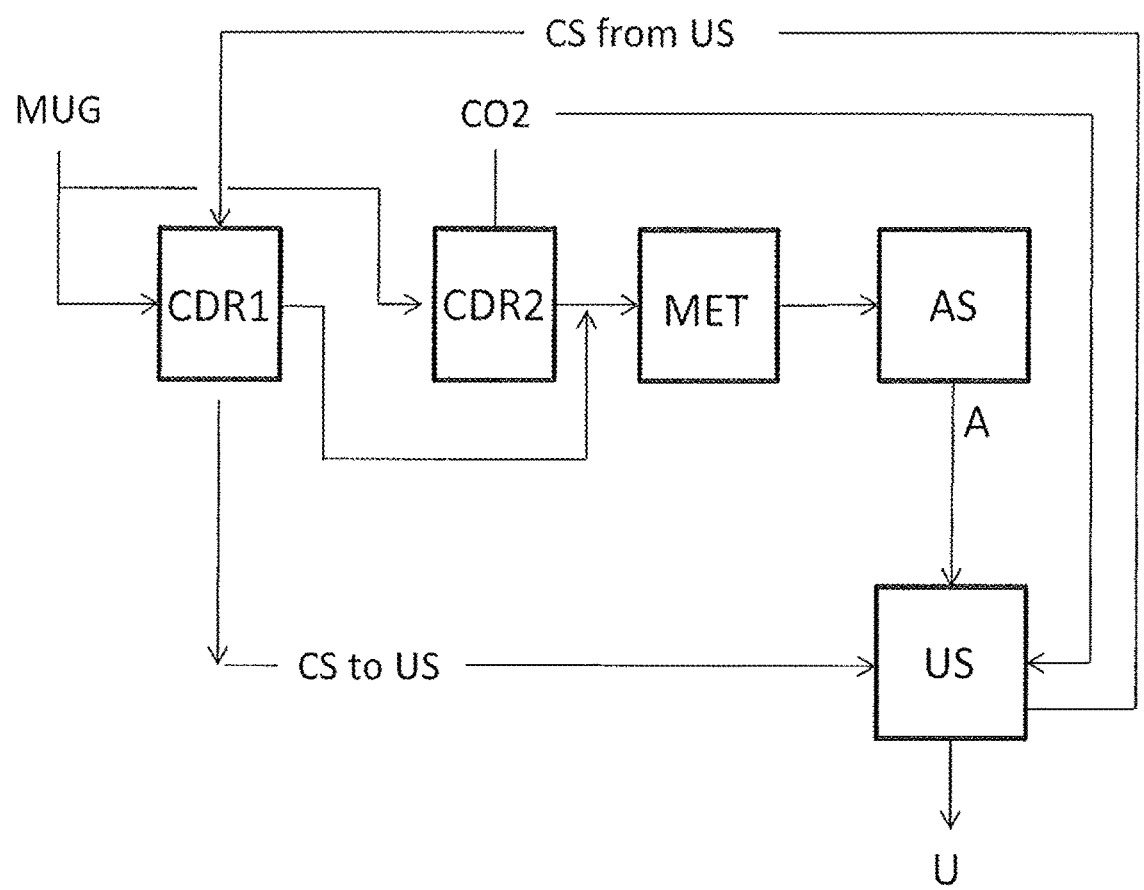
FIG. 3 is a scheme of a third embodiment of the invention.

FIG. 3 shows an embodiment wherein the CO2 removal stages CDR1 and CDR2 are in parallel. Accordingly, a part of the make-up gas MUG goes to the first stage CDR1 and a remaining part goes to the second stage CDR2.

Figure 4:
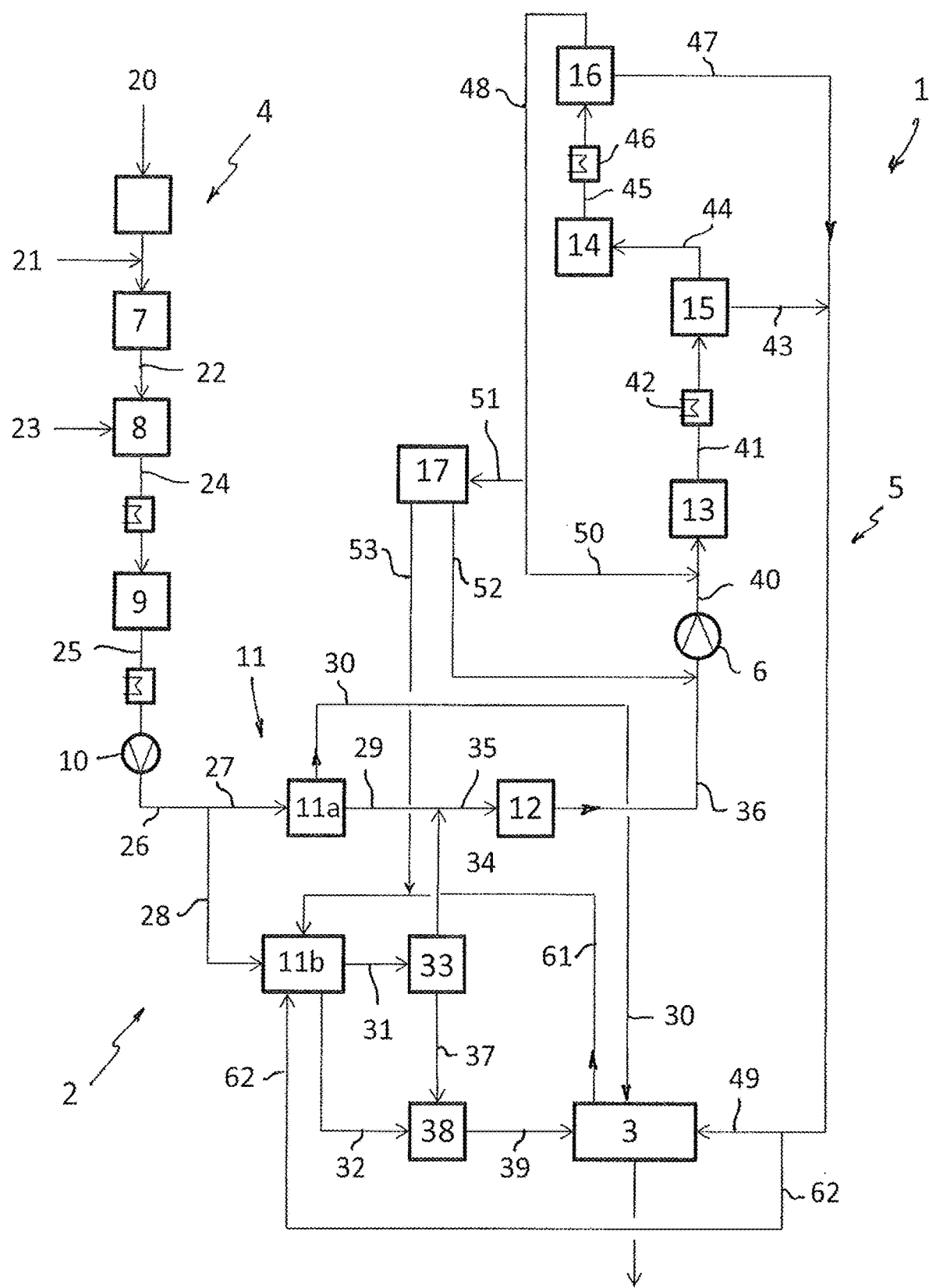
FIG. 4 is a scheme of an integrated ammonia-urea plant according to an embodiment of the invention.

FIG. 4 illustrates a parallel embodiment of the invention with a greater detail.

Referring to FIG. 4, an integrated ammonia-urea plant 1 comprises an ammonia section 2 and a urea section 3. The ammonia section 2 includes a reforming front-end 4 and a synthesis loop 5.

The reforming front-end 4 includes: primary reformer 7, secondary reformer 8, shift converter 9, low-pressure (LP) syngas compression stage 10, carbon dioxide removal section 11, methanator 12 and high-pressure (HP) syngas compression stage 6. The carbon dioxide removal section 11 includes stages 11a and 11b in parallel.

Natural gas 20 and steam 21 catalytically react in the primary reformer 7 to provide a partially reformed gas 22. Said partially reformed gas 22 further reacts in the secondary reformer 8 fired by an oxidant (e.g. air) 23. The fully reformed gas 24 leaving the secondary reformer 8 is treated in the shift converter 9 where CO is converted to CO2.

The shifted gas 25 is compressed in the LP compression stage 10. The compresses gas 26 delivered by said compression stage 10 is split into a first portions 27 and a second portion 28 which are treated respectively in the CO2 removal stages 11a and 11b.

In the first CO2 removal stage 11a, carbon dioxide is absorbed in a solution of a suitable absorbent and then stripped therefrom to provide a first CO2-depleted make-up gas 29 and a CO2 stream 30. Here the term "CO2 stream" denotes a gas stream composed predominantly of CO2.

In the second CO2 removal stage 11b (carbamate washing stage), the make-up gas 28 is contacted with a carbamate solution 61 taken from the tied-in urea section 3. A passivation agent (e.g. an oxygen carrier such as an oxygen-containing gas or hydrogen peroxide solution) may be added for corrosion protection and prevention.

FIG. 4 illustrates a preferred embodiment wherein the carbamate solution 61 is mixed with an aqueous ammonia solution 53 collected from a purge recovery section 17 of the ammonia synthesis loop 5. Accordingly, both streams 61 and 53 provide a washing medium to remove carbon dioxide from the syngas.

Additionally, an ammonia stream 62 is fed to the section 11b. This ammonia stream 62 allows to increase the absorption capability of the carbamate 61 and to deliver a CO2 depleted gas stream 31 containing only a negligible amount of unrecovered carbon dioxide.

The CO2 removal stage 11b produces a second CO2-depleted gas stream 31 and discharges a carbamate solution 32 which is sent back to the urea section 3 as further explained below. Preferably all the CO2 removed from the make-up gas 28 in the stage 11b is contained in the stream 32.

The second CO2-depleted gas stream 31 is cooled and sent to a washing column 33, wherein it is washed with water in order to remove traces of ammonia, thus providing a washed gas stream 34 which is joined with the above mentioned first gas portion 29 coming from the stage 11a.

The so obtained syngas 35 (now comprising the gas effluent from both stages 11a and 11b) is further treated in a methanator 12 for conversion of residual amounts of CO into methane.

The purified gas 36 effluent from said methanator 12 is sent to the HP compression section 6 to reach the ammonia synthesis pressure, e.g. 150 bar.

The carbamate solution 32 from stage 11b is sent to the urea section 3 together with ammonia 37 from bottom of said column 33 via a mixer 38. The resulting mixed flow 39 is sent to the urea section 3, preferably to the synthesis section. The solution 32 is advantageously cooled to a temperature above the crystallization temperature of the carbamate.

The synthesis loop 5 essentially comprises: a main reactor 13, a second reactor 14, a main loop HP separator 15, a second loop separator 16 and a purge recovery unit 17.

The compressed syngas 40 delivered by the HP compression stage 6 is joined with a stream of unreacted gas 50 and fed to the main reactor 13 where it partially reacts to give ammonia. The product gas 41 is cooled by a gas cooler 42 and passed through the main loop separator 15 which separates liquid ammonia 43 from unreacted gas 44.

Said unreacted gas 44 is fed to the second ammonia reactor 14 for further conversion. The resulting product gas 45 is cooled in a second gas cooler 46 and sent to the loop separator 16 which separates liquid ammonia 47 from unreacted synthesis gas 48.

The liquid streams 43 and 47 form the ammonia output. At least part of this ammonia output feeds the urea section 3 via line 49.

The unreacted gas 48 is split into portions 50 and 51. The first portion of unreacted gas 50 is recycled back to the main reactor 13 with the delivery stream 40 of the compressor 6, as above mentioned. The second portion of unreacted gas 51 is sent to the purge recovery unit 17, in particular for the recovery of hydrogen.

Said recovery unit 17 produces a stream 52 containing recovered hydrogen, which is sent to the suction side of compressor 6 together with the make-up gas 36, and the aqueous ammonia solution 53.

The urea section 3 receives ammonia from line 49 and carbon dioxide from lines 30 and 39, to produce urea 60. A part of the ammonia for the urea synthesis is contained in the stream 39 and it is supplied to the urea section 3 as stream 62 via the section 11b.

What is claimed is:

1. A process for the production of ammonia and urea in an ammonia-urea integrated plant comprising:
    reforming a hydrocarbon source to obtain a make-up gas containing hydrogen, $CO_2$, and nitrogen, wherein said make-up gas, after purification, is converted into ammonia in an ammonia synthesis section,
    at least part of the synthesized ammonia provides an ammonia feed of a urea synthesis process, said urea synthesis process also receiving a carbon dioxide feed,
    the urea synthesis process comprising the reaction of ammonia and carbon dioxide in a urea synthesis section to form a urea aqueous solution, and subsequent treatment of said solution in a urea recovery section that produces a carbamate solution,
    wherein the purification of the make-up gas comprises a first step of $CO_2$ removal in a first $CO_2$ removal unit and a second step of $CO_2$ removal in a second $CO_2$ removal unit, said first and second $CO_2$ removal units not being part of said urea synthesis section,
    one of said first and second $CO_2$ removal steps comprises washing the $CO_2$-containing make-up gas with the carbamate solution taken from said urea recovery section,
    said carbon dioxide feed of the urea synthesis process comprises at least part of the carbon dioxide separated from said make-up gas in the $CO_2$ removal steps, and
    wherein said $CO_2$ removal steps are carried out in series.

2. The process according to claim 1, further comprising introducing liquid or gaseous ammonia into the carbamate washing step.

3. The process according to claim 1, wherein the other of said $CO_2$ removal steps comprises absorption of $CO_2$ into an absorbing medium.

4. The process according to claim 1, wherein a portion of the $CO_2$-containing make-up gas admitted to said $CO_2$ removal steps bypasses the first $CO_2$ removal step of the series, and is sent directly to the subsequent $CO_2$ removal step.

5. The process according to claim 1, wherein the carbamate washing step is the first of the series.

6. The process according to claim 1, comprising a step of compression of the $CO_2$-containing make-up gas prior to said $CO_2$ removal steps, said make-up gas being compressed to an intermediate pressure lower than the ammonia synthesis pressure, wherein said $CO_2$ removal steps are carried out under said intermediate pressure.

7. The process according to claim 1, further comprising introducing an aqueous solution of ammonia into the carbamate washing step.

8. The process according to claim 7, wherein said aqueous solution of ammonia is obtained from treatment of a purge gas drawn from the ammonia synthesis section of the integrated ammonia-urea plant.

9. The process according to claim 1, wherein the conversion of the purified make-up gas into ammonia is carried out in at least a first synthesis and a second synthesis, wherein said first synthesis produces a first amount of ammonia and a first stream of unreacted make-up gas, and said unreacted make-up gas is converted in said second synthesis obtaining a second amount of ammonia and a second stream of unreacted make-up gas, and at least a portion of said second stream of unreacted make-up gas is recycled to said first synthesis.

* * * * *